United States Patent
Lazarini et al.

(10) Patent No.: US 11,504,049 B2
(45) Date of Patent: Nov. 22, 2022

(54) OLFACTORY MEANS USEFUL IN THE DIAGNOSIS AND TREATMENT OF MOOD DEPRESSION

(71) Applicants: INSTITUT PASTEUR, Paris (FR); CENTRE NATIONAL DE LA RECHERCHE SCIENTIFIQUE, Paris (FR)

(72) Inventors: Francoise Lazarini, Paris (FR); Pierre-Marie Lledo, Antony (FR); Eleni Siopi, Paris (FR); Raphael Servignat D'Aout, Clamart (FR)

(73) Assignees: INSTITUT PASTEUR, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 16/748,709

(22) Filed: Jan. 21, 2020

(65) Prior Publication Data
US 2020/0155055 A1  May 21, 2020

Related U.S. Application Data

(63) Continuation of application No. 14/784,226, filed as application No. PCT/EP2014/057277 on Apr. 10, 2014, now abandoned.

(30) Foreign Application Priority Data

Apr. 17, 2013 (EP) .................................. 13305499

(51) Int. Cl.
*A61B 5/00* (2006.01)
*A61B 5/16* (2006.01)

(52) U.S. Cl.
CPC ............ *A61B 5/4011* (2013.01); *A61B 5/165* (2013.01)

(58) Field of Classification Search
None
See application file for complete search history.

(56) References Cited

PUBLICATIONS

Borina Atanasova, Olfactory anhedonia and negative olfactory alliesthesia in depressed patients, 2010, Psychiatry Research, 176, pp. 190-196 (Year: 2010).*
Olga Pollatos, Reduced olfactory sensitivity in subjects with depressive symptoms, 2007, Journal of Affective Disorders, 102, pp. 101-108 (Year: 2007).*
Stephanie Kruger, Increased olfactory sensitivity in euthymic patients with bipolar disorder with event-related episodes compared with patients with bipolar disorder without such episodes, 2006, J Psychiatry Neurosci, 31(4), pp. 263-270 (Year: 2006).*
Naudin, Marine et al. "State and trait olfactory markers of major depression." PloS one vol. 7,10 (2012): e46938. doi:10.1371/journal.pone.0046938 (Year: 2012).*

(Continued)

*Primary Examiner* — Christian Jang
*Assistant Examiner* — Mitchell E Alter
(74) *Attorney, Agent, or Firm* — Arrigo, Lee, Guttman & Mouta-Bellum LLP

(57) ABSTRACT

A kit of two compositions comprising the same odorants in mixtures of different proportions is used for the measurement of olfactory discrimination capacity in subjects affected by a psychiatric disorder or disease involving mood disturbance, more particularly mood depression.

19 Claims, 7 Drawing Sheets

(56) References Cited

PUBLICATIONS

Hummel, T., et al., Normative data for the "SniYn Sticks" including tests of odor identification, odor discrimination, and olfactory thresholds: an upgrade based on a group of more than 3,000 subjects, Eur Arch Otorhinolaryngol (2007) 264:237-243.

Colle R et al. (2020). The olfactory deficits of depressed patients are restored after remission with venlafaxine treatment. Psychological Medicine 1-9. https://doi.org/10.1017/S0033291720003918.

* cited by examiner

OLFACTORY MEANS USEFUL IN THE DIAGNOSIS AND TREATMENT OF MOOD DEPRESSION

FIELD OF THE INVENTION

The application relates to olfactory means, more particularly to mixtures of odorants. The means of the application are notably useful in the diagnosis and in the treatment of psychiatric disorders or diseases involving mood disturbance, more particularly mood depression.

BACKGROUND OF THE INVENTION

Olfaction is known to be closely related to emotional processes and mood. However, little is known about the role of odor impairment in psychiatric disorders involving mood disturbances, more particularly mood depression. Depressive disorders, depressions, major depressive episode(s) and Major Depressive Disorders (MDD) are highly prevalent and debilitating conditions, associated with significant mortality and extraordinary costs for the society. Selective Serotonin Reuptake Inhibitors (SSRI) and Serotonin and Noradrenalin Reuptake Inhibitors (SNRI) are the most commonly prescribed antidepressant drugs, more particularly for the treatment of MDD. Yet, 60% of major depressive episodes do not respond adequately and 20-30% of them are resistant to SSRI/SNRI, defining treatment resistant depression.

Pause et al. 2001 (Journal of Psychiatric Research 35: 271-277) relates to olfactory sensitivity and odor evaluations in a homogenous sample of unipolar depressive patients compared to healthy control subjects. Olfactory sensitivity is determined by a detection test that uses serial dilutions of propanediol. Odor evaluations are subjective ratings of odor valence and intensity performed with pure odorants. The pure odorants are presented for smelling or sniffing as individual odorants (e.g., a bottle containing eugenol (clove scent), another bottle containing isoamylacetate (banana scent), etc.). Pause et al. 2001 observes that:
- olfactory sensitivity, as measured by the threshold test, is strongly reduced in patients with severe depression, and that after successful treatment, this loss in sensitivity is reduced and does not significantly differ from the control level, but that
- the subjective odor evaluations are not markedly changed in general.

Pollatos et al. 2007 (Journal of Affective Disorders 102: 101-108) relates to olfactory perception in subjects with varying degrees of depressive symptoms (depressive symptoms ranging from score zero to score nine according to the BECK DEPRESSION INVENTORY® scoring system). Olfactory perception included olfactory sensitivity and olfactory discrimination capacity. Olfactory sensitivity and olfactory discrimination capacity were measured using the odor threshold test and the odor discrimination test, respectively, which are described in Hummel et al. 1997 (Chem. Senses 22: 39-52). Said tests use pen-like odor dispensing devices, i.e., sniffing sticks, containing and releasing pure odorants. The odor threshold test uses serial dilutions of n-butanol to record the dilution at which the subject starts discerning the odorant. The odor discrimination test is performed by presenting to the subject three sniffing sticks each containing one odorant. Two of the three sticks contain the same odorant (e.g., isoamylacetate (banana scent)), while the third stick contains a different odorant (e.g., anethol (aneth scent)). The task of the subject is to identify the stick that has a different smell. Pollatos et al. 2007 observes that the degree of depressive symptoms negatively correlates with the odor detection threshold value (olfactory sensitivity), while olfactory discrimination is not related to the degree of depressive symptoms.

The inventors demonstrate that, contrary to what could be expected or inferred from the prior art, olfactory discrimination is significantly reduced in depressed subjects. The loss in olfactory discrimination capacity is observed by submitting the depressed subject to mixtures containing at least two different odorants.

SUMMARY OF THE INVENTION

The present application relates to the subject-matter as defined in the claims as filed and as herein described.

The means of the application are notably useful in the field of psychiatric disorders involving mood disturbances, more particularly psychiatric disorders involving mood depression, such as depressive disorders, depressions, depressive disorders, major depressive episode(s) and Major Depressive Disorders (MDD).

The means of the application comprise at least one mixture of odorants or at least one composition comprising odorants in mixture. Said odorants consist of at least two different odorants, more particularly of two different odorants.

The means of the application more particularly comprise the functional association of at least two different mixtures or compositions of the application. The odorants are the same in each mixture or composition that belongs to the same functional association, but at least one of said at least two mixtures or compositions contains said odorants in (a) proportion(s) that differ(s) from the other mixture(s) or composition(s) of the same functional association.

A reduction in the capacity to identify within at least one functional association the at least one mixture or composition, which contains the odorants at different proportion(s) compared to the other mixture(s) or composition(s) of the said at least one functional association, is indicative of, or positively correlates with, a diagnosis of psychiatric disorder involving mood disturbance, more particularly mood depression. More particularly, the reduction in said capacity is indicative of, or positively correlates with the severity of the psychiatric disease and/or with non-response (or resistance) to antidepressant treatment.

The means of the application further comprise the collection of at least two (different) functional associations of the application, as well as kits comprising at least mixture or composition of the application, or at least two different mixtures or compositions of the application, or least one functional association of the application, or at least two different functional associations of the application.

The application also relates to the biotechnological or medical applications of the means of the application, notably in the field of the diagnosis and/or treatment of psychiatric disorders involving mood disturbances, more particularly psychiatric disorders involving mood depression.

last bar (at the bottom)=CORT, followed by CORT+ fluoxetine (FLX or fix).

C57BL/6 male mice from Taconic Farms, Inc. (Tornbjergvej 40, DK-4623 Lille Skensved, Denmark) were administered corticosterone (CORT, 5 mg/kg/day in drinking water) for one month, to induce an anxiety/depression-like state. Depression-like behavior was checked by the splash test, the open field test, elevated plus maze and novelty suppressed feeding.

Then, 29 of these mice were put on a chronic fluoxetine regimen (FLX: 5 mg/kg/day in drinking water, with CORT, 5 mg/kg/day, named CORT+FLX mice) [cf. last bar of the diagram], while 8 mice continued to receive corticosterone chronically (named CORT mice) [cf. penultimate bar of the diagram]. Moreover, 8 control mice received the vehicle only (named VEHICLE mice) [cf. first bar of the diagram].

Figure 2:
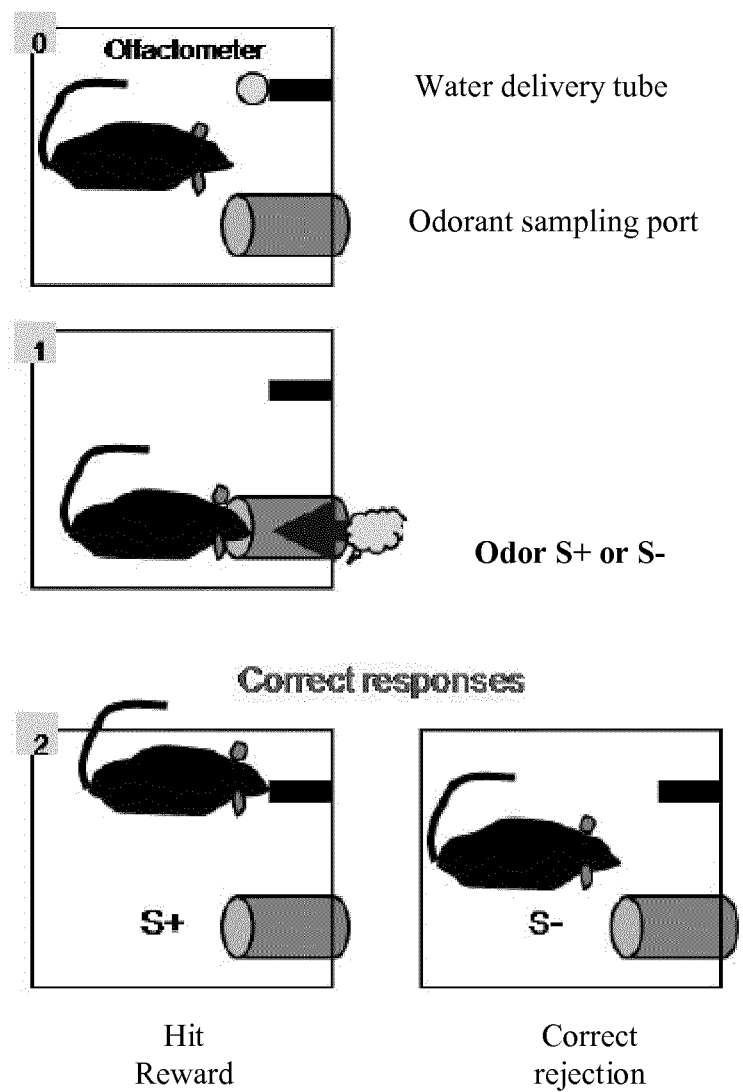

FIG. 2: Mice are trained in olfactometers to discriminate between 2 odorants: a positive stimulus (S+) and a negative stimulus (S−). The olfactometer cage contains an odorant sampling port to inject odorants inside the cage, and a water delivery tube to reward partially water-deprived animals (0) and (1). Cages are ventilated for fast odorant removal. When S+odorant is injected through the sampling port, the mouse should go to the water delivery tube and hit it, resulting in water reward (Correct answer: (2), left panel). If the mouse does not hit the water delivery tube it will not be rewarded (Error: miss). When S-odorant is injected into the cage, the mouse should not hit the water delivery tube (Correct answer: (2), right panel) since it will not be rewarded (Error: false alarm).

TABLE 1

| Correct Error | Go out and lick | No lick |
|---|---|---|
| S+ | Hit Reward | Miss |
| S− | False alarm | Correct rejection |

Figures 3A, 3B, 3C:
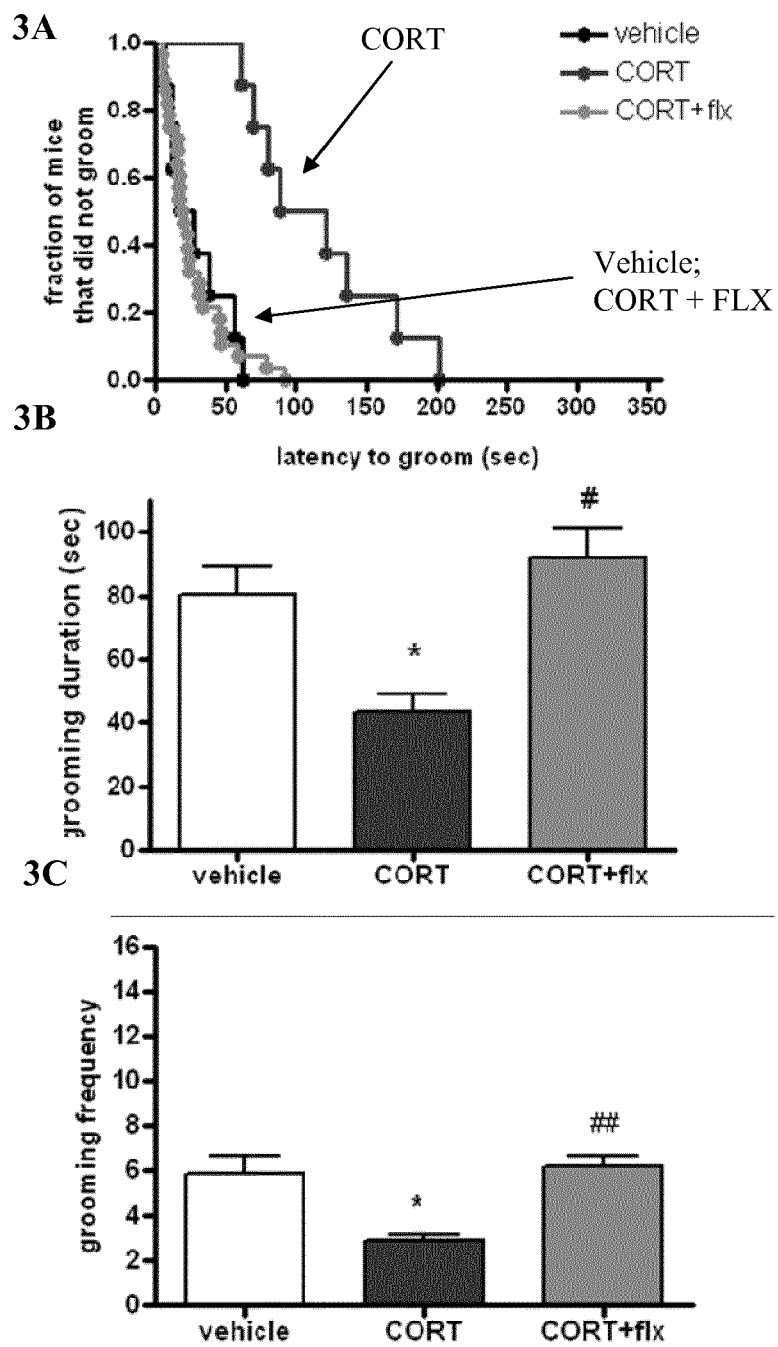

FIGS. 3A, 3B and 3C: Effects of chronic anti-depressant treatment on corticosterone-induced depression-like behavior in the splash test.

Results are expressed as the fraction of mice that did not groom within 6 minutes [FIG. 3A], mean grooming duration [FIG. 3B] and mean grooming frequency [FIG. 3C] following squirting of a 10% sucrose solution on the back coat of the mouse. Values plotted are mean±SEM (n=8/group in the vehicle and CORT group and n=28 in the CORT+flx group). CORT: corticosterone, fix: fluoxetine.

*: $P<0.05$ vs vehicle-treated, #: $P<0.05$ and ##: $P<0.01$ vs CORT-treated.

Figure 4A:
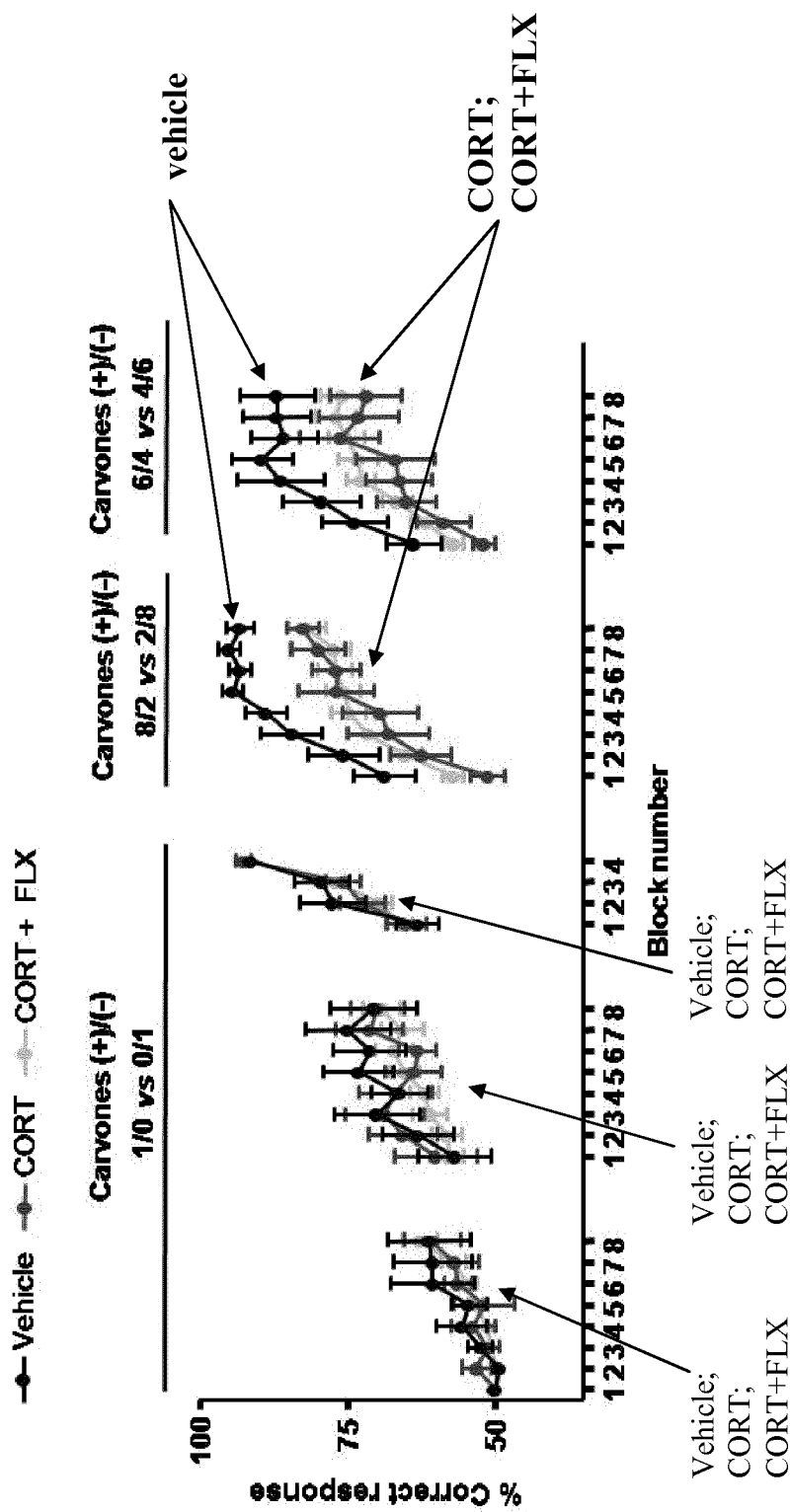
Figure 4B:
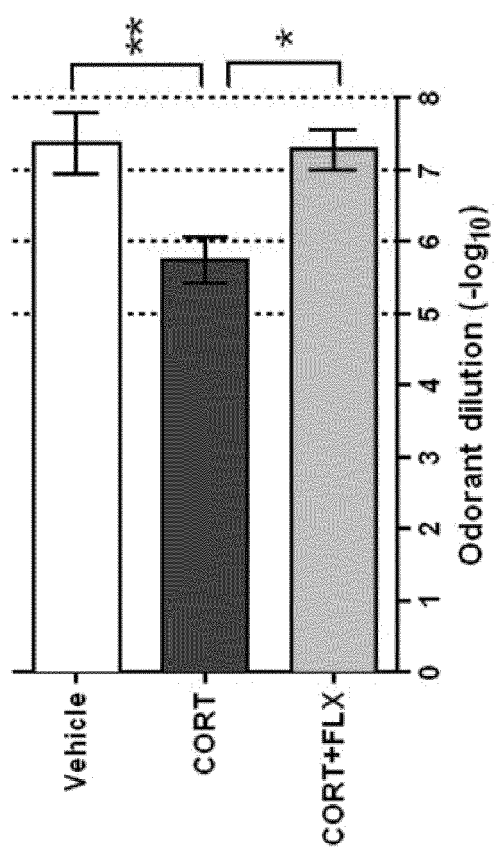

FIGS. 4A and 4B: Effects of chronic CORT and CORT+ fluoxetine administration on olfactory discrimination (FIG. 4A) and olfactory detection (FIG. 4B). Results are expressed as the mean±SEM of correct response (a) or detection thresholds ($-\log_{10}$ of odorant dilution). *: $P<0.05$, **: $P<0.01$.

Figure 5A:
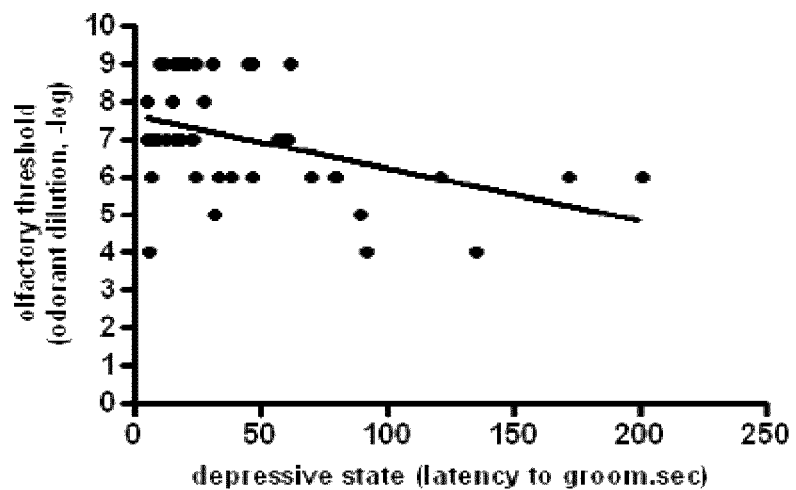
Figure 5B:
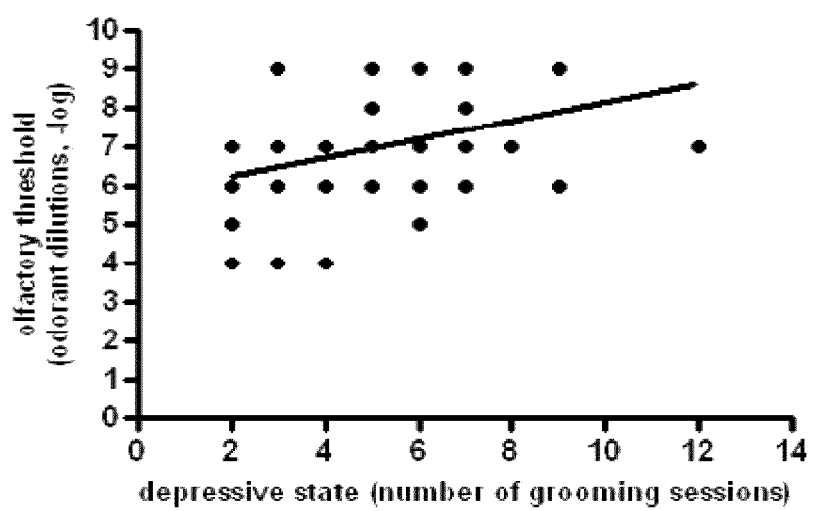

FIGS. 5A and 5B: Scatter plot between depressive state (latency to groom [FIG. 5A] and number of grooming sessions [FIG. 5B] in the splash test) and olfactory detection.

FIG. 5A: $r^2=0.18$; $P=0.004$; n=44;
FIG. 5B: $r^2=0.13$; $P=0.017$; n=43.

Figure 6A:
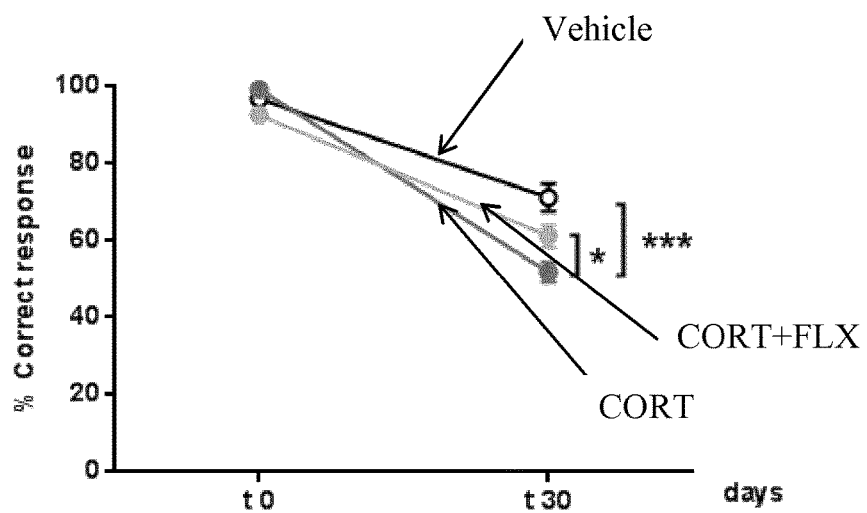
Figure 6B:
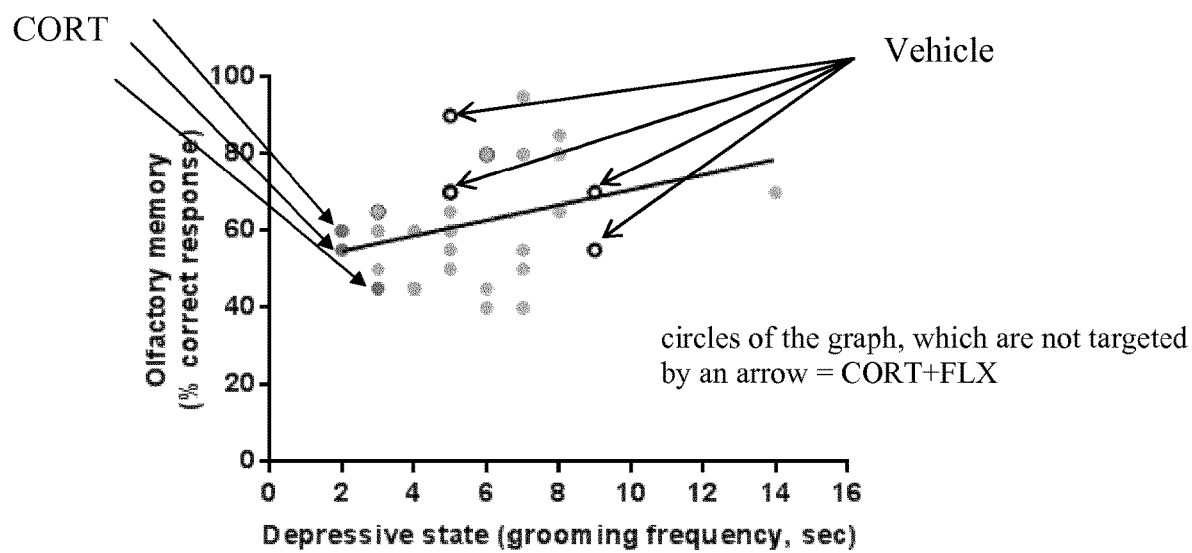

FIGS. 6A and 6B: Graph depicting performance at the long-term olfactory memory test (% correct response in the last block of training (acquisition: t0) and in the first block of testing (memory test: t30) (FIG. 6A)) and scatter plot between depressive state (grooming frequency in the splash test) and long-term olfactory memory (FIG. 6B). FIG. 6A: Results are expressed as the mean±SEM of correct response (n=8/group in the vehicle and CORT group and n=35 in the CORT+FLX group). ***$P<0.001$ between vehicle and CORT-treated, *$P<0.05$ between CORT and CORT+FLX FIG. 6B: $r^2=0.11$; **$P=0.03$; n=42

CORT: corticosterone, FLX: fluoxetine, t: time (day)

DETAILED DESCRIPTION OF THE INVENTION

The present application relates to the subject-matter as defined in the claims as filed and as herein described.

The application demonstrates that, contrary to what could be expected or inferred from the prior art, olfactory discrimination is significantly reduced in subjects affected by psychiatric disorders or diseases involving mood disturbance, more particularly mood depression.

In the application, said psychiatric disorders or diseases notably encompass depressive disorders and depression, more particularly depressive episode(s), major depressive episode(s) and Major Depressive Disorders (MDD).

In the application, the terms "psychiatric disorder", "psychiatric disease", "mood disturbance", "mood depression", "depressive disorder", "depression", "major depressive episode" and "Major Depressive Disorder" have their respective ordinary meanings in the field.

Please see, for example, the Diagnostic and Statistical Manual of Mental Disorders (DSM), edited by the American Psychiatric Association (1000 Wilson Boulevard, Suite 1825, Arlington, Va. 22209-3901, U.S.A.; http://www.psychiatry.org/home), e.g., the DMS-IV-TR edition (fourth edition, text revision, published in July 2000) or the DSM-V edition, which is to be published in 2013 [cf. http://psychiatryonline.org/].

Please see, for example, the BECK DEPRESSION INVENTORY® (BDI), more particularly the BDI-II edition published in 1996 (Beck, A. T., Steer, R. A., & Brown, G. K. 1996, Manual for the Beck Depression Inventory-II. San Antonio, Tex.: The Psychological Corporation, U.S.A.).

The application shows that said loss in olfactory discrimination capacity is observed by submitting the subject to mixtures containing at least two different odorants, more particularly to mixtures containing said at least two different odorants in different proportions.

More particularly, the application demonstrates that a subject affected by a psychiatric disorder or disease involving mood disturbance, more particularly mood depression, has a lower capacity to discriminate a mixture, which contains at least two different odorants in a certain proportion, from a mixture, which contains the same at least two different odorants but in a different proportion. The application further demonstrates that said loss in olfactory discrimination capacity is not restored by standard SSRI/SNRI treatment, such as fluoxetine treatment (PROZAC®). FIG. 4A illustrates this demonstration.

The application also provides a demonstration, which relates to the olfactory detection capacity, i.e., the threshold concentration at which a subject stops or starts detecting one (mono-)odorant (the threshold test is performed by serial dilution of a single odorant, which is not mixed with any other odorant). The application demonstrates that the olfactory detection capacity is decreased in a subject affected by a psychiatric disorder or disease involving mood disturbance, more particularly mood depression, but is restored by standard SSRI/SNRI treatment, such as fluoxetine treatment (PROZAC®). FIG. 4B illustrates this demonstration.

Hence, the application demonstrates that:
both the olfactory detection capacity and the olfactory discrimination capacity are decreased in a subject affected by a psychiatric disorder or disease involving mood disturbance, more particularly mood depression, and that
standard SSRI/SNRI treatment, such as fluoxetine treatment (PROZAC®), may restore the olfactory detection threshold, but does not restore the olfactory discrimination capacity. The terms "olfactory detection threshold", "olfactory discrimination" and "olfactory discrimination capacity" are intended in accordance with their respective ordinary meanings in the field. Please see e.g., Hummel et al. 1997 (Chem. Senses 22: 39-52).

As above mentioned (and below illustrated), the demonstration of the application notably stems from the fact that the inventors have overcome a prejudice in the art, more particularly concerning olfactory discrimination capacity (cf. background section), and from the conception and reduction to practice of an improved olfactory discrimination test, which involves mixtures comprising at least two different odorants in different proportions. The means of the application have the further advantage of being non-invasive means.

The application therefore relates to a mixture of odorants and to a composition comprising odorants in mixture. Said odorants consists of at least two different odorants, more particularly of two different odorants.

Said two, or at least two, odorants may be in, in mixture with, a (pharmaceutically-acceptable) vehicle, more particularly a vehicle, which is perceived to be odorless by mammals, or by at least one mammal race or species, advantageously at least by humans (i.e., no odor and no scent perceived by olfactory cognition). Advantageously, said vehicle does not alter the odor or scent emitted by each of said two, or of said at least two, odorants. More particularly, said vehicle is structurally suitable for homogeneously mixing said two, or said at least two odorants, together, such as e.g., a solvent, a cream or a paste. Advantageously, said vehicle is a solvent. More particularly, said vehicle is an odorless liquid solvent, such as water, mineral oil or propylene glycol.

A mixture or composition of the application can be comprised on or in a device or instrument for dispensing odor or scent, more particularly for olfactory testing. The application therefore relates to a device or instrument for dispensing odor or scent, more particularly for olfactory testing, which comprises a mixture or composition of the application. The device or instrument of the application comprises a structure for dispensing the odor(s), scent(s) or smell(s) emitted by the mixture or composition of the application, which is comprised in or on said device or instrument. More particularly, the structure of the device or instrument of the application is adapted, or especially adapted, to sniffing or smelling by a mammal, more particularly to active sniffing or smelling by a mammal. More particularly, the structure of the device or instrument of the application is adapted, or especially adapted, to allow for a mammal to [actively] sniff or smell the odor(s), scent(s) or smell(s) emitted by said mixture or composition.

In the application, the term "mammal" means any mammal, more particularly a non-human mammal, such as a rodent (more particularly a mouse), or a human, still more particularly a diseased non-human mammal or a diseased human, even still more particularly a diseased non-human mammal or a diseased human affected by or suspected of being affected by a psychiatric disorder or disease involving mood disturbance, more particularly mood depression.

According to a particular embodiment of the application, the term "mammal" means a human, more particularly a diseased human, still more particularly a diseased human affected by or suspected of being affected by a psychiatric disorder or disease involving mood disturbance, more particularly mood depression.

More particularly, the olfactory device or instrument of the application is an odor dispensing device for assessing nasal chemosensory performance. It can function as a fully extra-nasal or extra-nostril device or instrument, or as a (partially) intra-nasal or intra-nostril device or instrument.

Devices or instruments for dispensing odor or scent, more particularly for olfactory testing are available to the person of ordinary skill in the art. They include the olfactory devices or instruments that are used in:
the "University of Pennsylvania Smell Identification Test" (UPSIT) [Doty et al. 1984, Physiol. Behav. 32: 489-502; Doty et al. 1984, Laryngoscope 94 (2Pt1): 176-178], commercialized e.g., by Sensonics, Inc. (P.O. Box 112 Haddon Heights, N.J. 08035, USA) as the "Smell Identification TestT",
its down-scaled version the "Cross Cultural Smell Identification Test" (CC-SIT) [Doty et al. 1996, Laryngoscope 106 (3Pt1): 353-356],
the "Connecticut Chemosensory Clinical Research Center Test" (CCCRC) [Cain et al. 1988, Laryngoscope 98:83-88; Cain 1989, Ear Nose Throat J. 68: 316, 322-328], and
the olfactory test battery "SNIFFIN' STICKS™" [Kobal et al. 1996, Rhinology 34: 222-226; Hummel et al. 1997, Chem. Senses 22: 39-52; Kobal et al. 2000, Eur. Arch. Otorhinolaryngol. 257: 205-211; Hummel et al. 2001, Ann. Otol. Rhinol. and Laryngol. 110: 976-981; Hummel et al. 2007, Eur. Arch. Otorhinolaryngol. 364(3): 237-243], commercialized e.g., by Burghardt Messtechnik GmbH (Tinsdaler Weg 175, D-2280 Wedel, Germany; cf. commercial references LA-13-00134, LA-13-00136, LA-13-00138, LA-13-00135 and LA-13-00137; http://www.burhart-mt.de).

The olfactory devices or instruments that are used in tests such as the UPSIT and the CC-SIT test comprise a plurality of cards or booklet pages, which each contain one odorant (or a control substance) embedded therein, e.g., by microencapsulation with a binder. The odorant is released by scratching a surface of the card or page.

The olfactory devices or instruments that are used in tests such as the CCCRC test comprise a plurality of bottles or jars, e.g., of polyethylene bottles, which each contain one odorant (or a control substance), e.g., an odorant in liquid form. The bottle or jar is generally provided with a pop-up spout that fits to one or both nostrils and dispenses the odorant to the sniffing user.

The olfactory devices or instruments that are used in tests such as the SNIFFIN' STICKS™ test comprise a plurality of capped felt-tip pens, which each contain one odorant (or a control substance) in a reservoir or absorbent material that is associated with the felt tip of the pen. The pen is de-capped to place the felt tip at a few centimeters from the nostrils (e.g., at about 2 cm), and to smell or sniff the odorant dispensed through the felt tip.

Therefore, examples of an olfactory device or instrument of the application comprise any structure, which can function as a reservoir for odorants and as a dispenser of said odorants, such as:

an absorbent material, more particularly an absorbent fibrous and/or cellulosic material, such as a filter, card or page, optionally provided with microcapsules suitable for entrapping the odorants, a bottle or jar, e.g., a polyethylene bottle, optionally provided with a pop-up spout that fits to one or both nostrils, a pen-like dispensing device, such as a felt-tip pen of said "SNIFFIN' STICKS™" battery.

Advantageously, the structure of the device is adapted to, or especially adapted to, the assessment of nasal chemosensory performance, more particularly the assessment of nasal chemosensory performance of a human.

An odorant is any substance or compound that emits an odor or scent, or any substance or compound that has a distinctive smell. An odor, scent or smell is the odor, scent or smell that is consciously perceived by a mammal by smelling or sniffing though the nostril(s) (olfactory cognition).

Advantageously, an odorant is a substance or compound, which is identifiable (by olfactory cognition) by said mammal, more particularly by the human population to which the odorant is intended, more particularly by a human.

An odorant can be a substance or compound, which is volatile and/or hydrophobic, advantageously volatile and hydrophobic.

Advantageously, an odorant is a substance or compound, which is generally recognized as safe to mammals, more particularly to humans.

Advantageously, an odorant is a compound, more particularly a monomolecular compound.

According to an aspect of the application, each of said at least two odorants, more particularly each of said two odorants, is a monomolecular compound, more particularly a monomolecular compound, which is identifiable by a human by olfaction cognition, still more particularly a monomolecular compound, which is volatile, hydrophobic and identifiable by a human by olfaction cognition, even still more particularly a monomolecular compound, which is volatile, hydrophobic, identifiable by a human by olfaction cognition and generally recognized as safe to humans.

The expression "different odorants" means odorants, which emit different odors or scents. Hence, an odorant is different from another odorant if it emits an odor or scent that is different or perceived to be different from said other odorant. More particularly, an odorant is different from another odorant if the majority of a representative number of normosmic healthy mammals belonging to the same mammal race or species perceives that they emit different odors or scents. For example, an odorant is different from another odorant if more than 40% of a representative number of normosmic healthy mammals belonging to the same mammal race or species perceive that they emit different odors or scents. More particularly, said percentage is more than 45%, more particularly more than 50%, more particularly more than 55%, more particularly more than 60%, more particularly more than 65%. A representative number of normosmic healthy mammals belonging to the same mammal race or species can be determined by the person of ordinary skill in the art depending on the mammal race or species being tested. Such a number generally is more than 10, more particularly more than 20.

According to an aspect of the application, each of said at least two odorants, more particularly each of said two odorants, is a monomolecular compound emitting an odor or scent (as perceived by a healthy normosmic human) selected from the group consisting of anise, apple, banana, caramel, chocolate, cinnamon, clove, cocoa, coconut, coffee, cola, dill, *eucalyptus*, fish, flower, honey, garlic, ginger, grapefruit, grass, lavender, leather, lemon, lilac, lily of the valley, licorice, melon, mint, mushroom, onion, orange, peach, pear, peppermint, pineapple, rose, spearmint, turpentine, raspberry, sesame oil, smoked meat, soy sauce and vanilla.

According to an aspect of the application, each of said at least two odorants, more particularly each of said two odorants is a monomolecular compound emitting an odor or scent (as perceived by a healthy normosmic human) selected from the group consisting of anise, banana, clove, dill and spearmint.

Examples of monomolecular compounds emitting such an odor or scent comprise:

R-carvone (or L-carvone or carvone −), for spearmint odor or scent,

S-carvone (or D-carvone or carvone +), for dill odor or scent, isoamylacetate or n-butanol, more particularly isoamylacetate, for banana odor or scent, anethol, for anise odor or scent, eugenol, for clove odor or scent, 2-phenylethanol for rose odor or scent, geraniol for rose odor or scent, linalool for lily of the valley odor or scent, cineole for *eucalyptus* odor or scent, D-limonene (or R-limonene or limonene +) for orange odor or scent, L-limonene (or S-limonene or limonene −) for turpentine odor or scent, menthol for mint odor or scent, and cinnamon aldehyde for cinnamon odor or scent.

Please see e.g., the Arctander atlas (Arctander S. "*Perfume and flavor chemicals*: (*aroma chemicals*)", Allured Publishing Corporation, Carol Stream Ill., 1994).

Please also see the OdorDB database (Yale Center for Medical Informatics, U.S.A.) available on http://senselab.med.yale.edu/odordb/eavObList.aspx?db=5&c1=1.

According to an aspect of the application, each of said at least two odorants, more particularly each of said two odorants is a monomolecular compound selected from the group consisting of R-carvone, S-carvone, isoamylacetate, anethol and eugenol.

As mentioned above, each of said at least two odorants, or each of said two odorants, are different from each other. For example:

one of said at least two, or of said two, odorants is a monomolecular compound emitting spearmint odor or scent (e.g., R-carvone), and the other of said at least two, or of said two, odorants is:

a monomolecular compound emitting dill odor or scent (e.g., S-carvone) or a monomolecular compound emitting banana odor or scent (e.g., isoamylacetate)

or a monomolecular compound emitting anise odor or scent (e.g., anethol) or a monomolecular compound emitting clove odor or scent (e.g., eugenol), or one of said at least two, or of said two, odorants is a monomolecular compound emitting dill odor or scent (e.g., S-carvone), and the other of said at least two, or of said two, odorants is a monomolecular compound emitting spearmint odor or scent (e.g., R-carvone) or a monomolecular compound emitting banana odor or scent (e.g., isoamylacetate)
or
a monomolecular compound emitting anise odor or scent (e.g., anethol) or
a monomolecular compound emitting clove odor or scent (e.g., eugenol),
or
one of said at least two, or of said two, odorants is a monomolecular compound emitting banana odor or scent (e.g., isoamylacetate), and the other of said at least two, or of said two, odorants is
a monomolecular compound emitting dill odor or scent (e.g., S-carvone) or
a monomolecular compound emitting spearmint odor or scent (e.g., R-carvone) or
a monomolecular compound emitting anise odor or scent (e.g., anethol) or
a monomolecular compound emitting clove odor or scent (e.g., eugenol),
or
one of said at least two, or of said two, odorants is a monomolecular compound emitting anise odor or scent (e.g., anethol), and the other of said at least two, or of said two, odorants is
a monomolecular compound emitting dill odor or scent (e.g., S-carvone) or
a monomolecular compound emitting banana odor or scent (e.g., isoamylacetate)
or
a monomolecular compound emitting spearmint odor or scent (e.g., R-carvone) or
a monomolecular compound emitting clove odor or scent (e.g., eugenol),
or
one of said at least two, or of said two, odorants is a monomolecular compound emitting clove odor or scent (e.g., eugenol), and the other of said at least two, or of said two, odorants is
a monomolecular compound emitting dill odor or scent (e.g., S-carvone) or
a monomolecular compound emitting banana odor or scent (e.g., isoamylacetate)
or
a monomolecular compound emitting anise odor or scent (e.g., anethol) or
a monomolecular compound emitting spearmint odor or scent (e.g., R-carvone).

In a mixture or composition of the application, said at least two odorants, or said two odorants, are contained in mixture and in any proportion that the person of ordinary skill in the art finds appropriate.

For example, said at least two odorants, or said two odorants, are contained in the mixture or composition of the application in a proportion ranging from 1:1 to 1:5, more particularly in a proportion ranging from 1:1.5 to 1:4, for example in a proportion of 1:1.5, 1:2, 1:2.5, 1:3, 1:3.5 or 1:4. A "X:Y" proportion means X part(s) of one of said at least two, or of said two, odorants for Y part(s) of the other of said at least two, or of said two, odorants (X and Y can identical or different). Said part values are volume parts or weight parts, more particularly volume parts.

For example, said at least two odorants, or said two odorants, are contained in the mixture or composition of the application in a proportion ranging from 0.8%/0.2% to 0.2%/0.8% to 0.2%/0.8%, more particularly in a proportion ranging from 0.6%/0.4% to 0.4%/0.6%, for example in a proportion of 0.8%/0.2%, 0.6%/0.4%, 0.4%/0.6% or 0.2%/0.8%. A proportion of "X %/Y %" means X % of one of said at least two, or of said two, odorants and Y % of the other of said at least two, or of said two, odorants. A % value of an odorant is the volume or weight, more particularly the volume, of said odorant expressed with respect to the total volume or weight of the mixture in said mixture, more particularly to the total volume of said mixture.

For example, said at least two odorants, or said two odorants, are contained in the mixture or composition of the application in a proportion ranging from 8/2 to 2/8, more particularly in a proportion ranging from 6/4 to 4/6, for example in a proportion of 8/2, 6/4, 4/6 or 2/8. A proportion of "X/Y" means a concentration of X of one of said at least two, or of said two, odorants and a concentration of Y of the other of said at least two, or of said two, odorants. The concentrations X and Y are expressed in the same unit, for example in volume/volume percent, in volume/weight percent or in weight/weight percent, more particularly in volume/volume percent, and are expressed with respect to the total volume or weight of the mixture in said mixture, more particularly to the total volume of said mixture.

More particularly, the application relates to the functional association of several (different) mixtures or compositions of the application for sequential use. Each of said several mixtures can be (separately) comprised in or on a device or instrument for dispensing odor or scent as above-described (and as below-illustrated).

In a functional association of the application, said several (different) mixtures or compositions are (and remain) distinct or separate from each other. Hence, when they are contained in or on a device or instrument for dispensing odor or scent, they are not mixed together. Advantageously, they are not contained in the same device or instrument. For example, each of said several mixtures or compositions is separately contained in an odor dispensing device for assessing nasal chemosensory performance as above-described (and as below-illustrated).

The odorants are the same in each mixture or composition that belongs to the same functional association, i.e., they are the same substances or compounds.

At least one of said several mixtures or compositions contains said odorants in a proportion that differs from the other mixture(s) or composition(s) of the same functional association.

Hence, the proportion of one of said (at least) two odorants with respect to the other of said (at least) two odorants in a first composition of an association is different from their proportion in at least one second composition of the same functional association.

Therefore, the application relates to a functional association, which comprises:
at least one first mixture or composition comprising odorants, wherein the odorants of said at least one first mixture or composition consist of (at least) two different odorants, and, separately or distinctly from said at least one first mixture or composition,
at least one second mixture or composition comprising odorants, wherein the odorants of said at least one second mixture or composition consist of (at least) two different odorants, wherein the odorants of said at least one first mixture or composition are the same compounds as the odorants of said at least one second mixture or composition, and wherein the proportion of said odorants (with respect to each other) in said at least one first mixture or composition is different from their proportion in said at least one second mixture or composition.

For example, the concentration of at least one odorant in said at least one first mixture or composition is different from its proportion in said at least one second mixture or composition.

For example, the respective concentrations of the (at least two) odorants in said at least one first mixture or composition are different from their respective concentrations in said at least one second mixture or composition.

According to an advantageous aspect of the application, said at least one first composition and said at least one second composition are for sequential use, more particularly for sequential use in the detection of olfactory discrimination impairment in a human, more particularly in a diseased human.

A functional association of the application may comprise any number of mixtures or compositions of the application that the person of ordinary skill in the art may find appropriate. For example, a functional association of the application may comprise two or three mixtures or compositions of the application.

For example, a functional association of the application comprises two or three mixtures or compositions of the application, which are distinct or separate from each other, wherein the odorants of said two or three mixtures or compositions are the same but are contained in one of said two or three mixtures or compositions in a proportion that differs from the remaining one or two mixtures or compositions. In the case of a number of three mixtures or compositions of the application, said remaining two mixtures or compositions can be identical, i.e., duplicate.

The application thus relates to a functional association, which comprises:
- a first composition comprising odorants, wherein the odorants of said first composition consist of at least two different odorants, and, separately or distinctly from said first composition,
- a second composition comprising odorants, wherein the odorants of said second composition consist of at least two different odorants, wherein said second composition is contained in duplicate.

The application thus relates to a functional association, which comprises:
- a first composition comprising odorants, wherein the odorants of said first composition consist of at least two different odorants, and, separately or distinctly from said first composition,
- a second composition comprising odorants, wherein the odorants of said second composition consist of at least two different odorants, and, separately or distinctly from said first composition and from said second composition,
- a third composition comprising odorants, wherein the odorants of said third composition consist of at least two different odorants, and wherein said third composition is a duplicate of said second composition.

Since said third composition is a duplicate of said second composition, the odorants of said second composition are the same compounds as the odorants of said third composition, and the proportion of the odorants with respect to each other in said second composition is identical to their proportion in said third composition.

Since said first composition belongs to the same functional association as said second and third compositions, the odorants of said first composition are the same compounds as the odorants of said second composition and as the odorants of said third composition, but the proportion of the odorants with respect to each other in said first composition is different from their proportion in said second composition and in said third composition.

Advantageously, the difference in proportions within the same functional association is sufficient to be distinguishable by a healthy normosmic human. Hence, according to an advantageous aspect of the application, the at least one mixture or composition, which contains said odorants in a proportion that differs from the other mixture(s) or composition(s) of the same association, is consciously perceived (olfactory cognition) as emitting an odor or scent that is different from the odor or scent emitted by the other mixture(s) or composition(s) of the association.

For example, a functional association of the application comprises (at least) two mixtures or compositions of the application, which are distinct or separate from each other, wherein the odorants of each of said (at least) two mixtures or compositions are the same two or the same at least two odorants, and wherein one of said two, or of said at least two, odorants is contained in one of said (at least) two mixtures or compositions in a 8/2 proportion, whereas the other of said two, or of said at least two, odorants is contained in the other of said (at least) two mixtures or compositions in a 2/8 proportion.

For example, a functional association of the application comprises three mixtures or compositions of the application, which are separate from each other (two of said three mixtures compositions being duplicate compositions as described above), wherein the odorants of each of said three mixtures or compositions are the same two or the same at least two odorants, and wherein one of said two, or of said at least two, odorants is contained in one of said three mixtures or compositions in a 8/2 proportion, whereas the other of said two, or of said at least two, odorants is contained in each of the two other (duplicate) mixtures or compositions in a 2/8 proportion.

For example, a functional association of the application comprises (at least) two mixtures or compositions of the application, which are distinct or separate from each other, wherein the odorants of each of said (at least) two mixtures or compositions are the same two or the same at least two odorants, and wherein one of said two, or of said at least two, odorants is contained in one of said (at least) two mixtures or compositions in a 6/4 proportion, whereas the other of said two, or of said at least two, odorants is contained in the other of said (at least) two mixtures or compositions in a 4/6 proportion.

For example, a functional association of the application comprises three mixtures or compositions of the application, which are separate from each other (two of said three mixtures compositions being duplicate compositions as described above), wherein the odorants of each of said three mixtures or compositions are the same two or the same at least two odorants, and wherein one of said two, or of said at least two, odorants is contained in one of said three mixtures or compositions in a 6/4 proportion, whereas the other of said two, or of said at least two, odorants is contained in each of the two other (duplicate) mixtures or compositions in a 4/6 proportion.

For example, a functional association of the application comprises (at least) two mixtures or compositions of the application, which are distinct or separate from each other, wherein the odorants of each of said (at least) two mixtures or compositions are R-carvone and S-carvone in mixture, and wherein one of said (at least) two mixtures or compositions contains R-carvone and S-carvone in a 8/2 proportion, whereas the other of said (at least) two mixtures or compositions contains R-carvone and S-carvone in a 2/8 proportion.

For example, a functional association of the application comprises three mixtures or compositions of the application, which are separate from each other (two of said three mixtures compositions being duplicate compositions as described above), wherein the odorants of each of said three mixtures or compositions are R-carvone and S-carvone in mixture, and wherein one of said three mixtures or compositions contains R-carvone and S-carvone in a 8/2 proportion, whereas each of the two other (duplicate) mixtures or compositions contains R-carvone and S-carvone in a 2/8 proportion.

For example, a functional association of the application comprises (at least) two mixtures or compositions of the application, which are distinct or separate from each other, wherein the odorants of each of said (at least) two mixtures or compositions are isoamylacetate and anethol in mixture, and wherein one of said (at least) two mixtures or compositions contains isoamylacetate and anethol in a 8/2 proportion, whereas the other of said (at least) two mixtures or compositions contains isoamylacetate and anethol in a 2/8 proportion.

For example, a functional association of the application comprises three mixtures or compositions of the application, which are separate from each other (two of said three mixtures compositions being duplicate compositions as described above), wherein the odorants of each of said three mixtures or compositions are isoamylacetate and anethol in mixture, and wherein one of said three mixtures or compositions contains isoamylacetate and anethol in a 8/2 proportion, whereas each of the two other (duplicate) mixtures or compositions contains isoamylacetate and anethol in a 2/8 proportion.

For example, a functional association of the application comprises (at least) two mixtures or compositions of the application, which are distinct or separate from each other, wherein the odorants of each of said (at least) two mixtures or compositions are anethol and eugenol in mixture, and wherein one of said two (at least) mixtures or compositions contains anethol and eugenol in a 8/2 proportion, whereas the other of said (at least) two mixtures or compositions contains anethol and eugenol in a 2/8 proportion.

For example, a functional association of the application comprises three mixtures or compositions of the application, which are distinct or separate from each other (two of said three mixtures compositions being duplicate compositions as described above), wherein the odorants of each of said three mixtures or compositions are anethol and eugenol in mixture, and wherein one of said three mixtures or compositions contains anethol and eugenol in a 8/2 proportion, whereas each of the two other (duplicate) mixtures or compositions contains anethol and eugenol in a 2/8 proportion.

The application also relates to a kit comprising at least one functional association of the application.

The application further relates to the collection of at least two (different) functional associations of the application for sequential use, more particularly to a kit comprising at least two functional associations of the application.

Said at least two (different) functional associations of the application are (and remain) distinct or separate from each other. The odorants of each of said at least two (different) functional associations can be the same compounds or different compounds. The proportions at which they are contained in each of said at least two (different) functional associations can be the same proportions or different proportions.

Hence, the application relates to the collection of:
at least one first mixture or composition comprising odorants, wherein the odorants of said at least one first mixture or composition consist of (at least) two different odorants,
at least one second mixture or composition comprising odorants, wherein the odorants of said at least one second mixture or composition consist of (at least) two different odorants,
at least one third mixture or composition comprising odorants, wherein the odorants of said at least one third mixture or composition consist of two different odorants,
at least one fourth mixture or composition comprising odorants, wherein the odorants of said at least one fourth mixture or composition consist of two different odorants,
wherein said at least one first, second, third and fourth mixtures or compositions are separate or distinct from each other,
wherein the odorants of said at least one first mixture or composition are the same compounds as the odorants of said at least one second mixture or composition, and
wherein the proportion of the odorants (with respect to each other) in said at least one first mixture or composition is different from their proportion in said at least one second mixture or composition,
wherein the odorants of said at least one third mixture or composition are the same compounds as the odorants of said at least one fourth mixture or composition, and
wherein the proportion of the odorants (with respect to each other) in said at least one third mixture or composition is different from their proportion in said at least one fourth mixture or composition.

The (at least two) odorants of said at least one first and second mixtures or compositions can be different from the (at least) two odorants of said at least one third and fourth mixtures or compositions.

The (at least two) odorants of said at least one first and second mixtures or compositions can be the same compounds as the (at least) two odorants of said at least one third and fourth mixtures or compositions, but in different proportions.

Said (at least one) second mixture or composition can be contained in duplicate, as described above. Said (at least one) fourth mixture or composition can be contained in duplicate, as described above.

For example, a kit of the application comprises at least one (first) functional association of the application, wherein the odorants are in 8/2 and 2/8 proportions, and at least one other (second) functional association, which comprises the same odorants as said first functional association but in different proportions, e.g., in 6/4 and 4/6 proportions. In each of said first and second associations, one of the (at least) two mixtures or compositions can be contained in duplicate (as above described).

For example, a kit of the application comprises at least one (first) functional association of the application, wherein the odorants are in 8/2 and 2/8 proportions, and at least one other (second) functional association, which comprises different odorants as said first functional association at the same or in different proportions, e.g., in 8/2 and 2/8 proportions or in 6/4 and 4/6 proportions. In each of said first and second associations, one of the (at least) two mixtures or compositions can be contained in duplicate (as above described).

For example, a kit of the application comprises
(at least) two mixtures or compositions of the application, which are distinct or separate from each other, wherein the odorants of each of said (at least) two mixtures or compositions are R-carvone and S-carvone in mixture, and wherein one of said (at least) two mixtures or compositions contain R-carvone and S-carvone in a 8/2 proportion, whereas the other of said (at least) two mixtures or compositions contain R-carvone and S-carvone in a 2/8 proportion (one of said (at least) two mixtures or compositions can be contained in duplicate, as above-described); and
(at least) two mixtures or compositions of the application, which are distinct or separate from each other, wherein the odorants of each of said (at least) two mixtures or compositions are R-carvone and S-carvone in mixture, and wherein one of said (at least) two mixtures or compositions contain R-carvone and S-carvone in a 6/4 proportion, whereas the other of said (at least) two mixtures or compositions contain R-carvone and S-carvone in a 6/4 proportion (one of said (at least) two mixtures or compositions can be contained in duplicate, as above-described).

For example, a kit of the application comprises:
(at least) two mixtures or compositions of the application, which are distinct or separate from each other, wherein the odorants of each of said (at least) two mixtures or compositions are R-carvone and S-carvone in mixture, and wherein one of said (at least) two mixtures or compositions contain R-carvone and S-carvone (e.g., in a 8/2 or 6/4 proportion), whereas the other of said (at least) two mixtures or compositions contain R-carvone and S-carvone (e.g., in a 2/8 or 6/4 proportion, respectively) (one of said (at least) two mixtures or compositions can be contained in duplicate, as above-described); and
(at least) two mixtures or compositions of the application, which are distinct or separate from each other, wherein the odorants of each of said (at least) two mixtures or compositions are isoamylacetate and anethol in mixture, and wherein one of said (at least) two mixtures or compositions contain isoamylacetate and anethol (e.g., in a 8/2 or 6/4 proportion), whereas the other of said (at least) two mixtures or compositions contain isoamylacetate and anethol (e.g., in a 2/8 or 6/4 proportion, respectively) (one of said (at least) two mixtures or compositions can be contained in duplicate, as above-described).

For example, a kit of the application comprises:
(at least) two mixtures or compositions of the application, which are distinct or separate from each other, wherein the odorants of each of said (at least) two mixtures or compositions are R-carvone and S-carvone in mixture, and wherein one of said (at least) two mixtures or compositions contain R-carvone and S-carvone (e.g., in a 8/2 or 6/4 proportion), whereas the other of said (at least) two mixtures or compositions contain R-carvone and S-carvone (e.g., in a 2/8 or 6/4 proportion, respectively) (one of said (at least) two mixtures or compositions can be contained in duplicate, as above-described); and
(at least) two mixtures or compositions of the application, which are distinct or separate from each other, wherein the odorants of each of said (at least) two mixtures or compositions are anethol and eugenol in mixture, and wherein one of said (at least) two mixtures or compositions contain anethol and eugenol (e.g., in a 8/2 or 6/4 proportion), whereas the other of said (at least) two mixtures or compositions contain anethol and eugenol (e.g., in a 2/8 or 6/4 proportion, respectively) (one of said (at least) two mixtures or compositions can be contained in duplicate, as above-described).

For example, a kit of the application comprises:
(at least) two mixtures or compositions of the application, which are distinct or separate from each other, wherein the odorants of each of said (at least) two mixtures or compositions are isoamylacetate and anethol in mixture, and wherein one of said (at least) two mixtures or compositions contain isoamylacetate and anethol (e.g., in a 8/2 or 6/4 proportion), whereas the other of said (at least) two mixtures or compositions contain isoamylacetate and anethol (e.g., in a 2/8 or 6/4 proportion, respectively) (one of said (at least) two mixtures or compositions can be contained in duplicate, as above-described); and
(at least) two mixtures or compositions of the application, which are distinct or separate from each other, wherein the odorants of each of said (at least) two mixtures or compositions are anethol and eugenol in mixture, and wherein one of said (at least) two mixtures or compositions contain anethol and eugenol (e.g., in a 8/2 or 6/4 proportion), whereas the other of said (at least) two mixtures or compositions contain anethol and eugenol (e.g., in a 2/8 or 6/4 proportion, respectively) (one of said (at least) two mixtures or compositions can be contained in duplicate, as above-described).

A mixture or composition of the application, more specifically a functional association or a kit of the application, or a collection of functional associations or a kit of the application, enables measuring the olfactory capacity of a mammal, more particularly the olfactory discrimination capacity of a mammal, more particularly detecting and/or measuring olfactory discrimination impairment in a mammal. More particularly, said mammal is a diseased mammal. More particularly, said mammal is a human, notably a diseased human, more particularly a diseased human affected by or suspected of being affected by a psychiatric disorder or disease involving mood disturbance, more particularly mood depression.

The several mixtures or compositions of a functional association of the application can be sequentially placed in smelling or sniffing contact with said mammal. The experimenter, laboratory technician or physician records whether said mammal succeeds in identifying, within the mixtures or compositions of the same association, the at least one mixture or composition that contains the (two, or at least two) odorants in a proportion that differs from the other mixture(s) or composition(s).

The person of ordinary skill in the art may appreciate that said sequential smelling or sniffing is advantageously performed under conditions that prevent or avoid olfaction contamination. For example, said sequential smelling or sniffing is advantageously performed in a room where aeration is sufficient to prevent or avoid olfaction contamination, and according to a time sequence, which prevents or avoids olfaction contamination from one mixture or composition to the next mixture or composition.

The person of ordinary skill in the art may appreciate that said sequential smelling or sniffing can be performed under blind testing.

If desired or required, said smelling or sniffing can be repeated with the same and/or with another functional association of the application.

A mixture or composition of the application, more specifically a functional association or a kit of the application, or a collection of functional associations or a kit of the application, can be further functionally associated with, or a kit of the application can further comprise any other additional element, such as at least one additional means, device, instrument, composition, substance or compound, that the person of ordinary skill in the art finds appropriate to measure olfactory capacity, more particularly to detect and/or measure olfactory impairment.

For example, said additional element can be means for measuring the olfactory detection threshold of a mammal or human, more particularly a diseased mammal or human.

Means for measuring olfactory detection threshold can for example comprise a plurality of compositions, wherein each composition of said plurality contains only one odorant, and wherein all the compositions of said plurality contains the same one odorant and form a serial dilution of said same one odorant.

Said odorant can be as defined above. For example, said odorant can be n-butanol or 2-phenylethanol. Please see Hummel et al. 1997, Chem. Senses 22: 39-52.

The application relates to the medical or biotechnological applications of at least one product of the application, i.e., at least one mixture or composition of the application, more specifically of at least one functional association, collection or kit of the application. Said applications comprise particularly methods and uses.

More particularly, a method or use of the application comprises the smelling or sniffing of at least one mixture or composition of the application, more particularly the sequential smelling or sniffing of at least two different mixtures or compositions of the application, more particularly the sequential smelling or sniffing of at least two different mixtures or compositions that belong to the same functional association as above-described (and below illustrated), more particularly of mixtures or compositions that belong to at least two different functional associations as above-described (and below) illustrated.

More particularly, said smelling or sniffing can be active smelling or sniffing.

A method or use of the application may notably comprise:
allowing at least one nostril of a subject to be in smelling or sniffing contact with at least one functional association of the application, and
determining and/or measuring the capacity of said subject to identify within said at least one functional association the at least one mixture or composition, which contains the odorants at different proportion(s) compared to the other mixture(s) or composition(s) of the said at least one functional association.

As above mentioned (and below illustrated), said smelling or sniffing, more particularly said sequential smelling or sniffing, allows for determining and/or measuring the olfactory capacity, more particularly the olfactory discrimination capacity, of the smelling or sniffing subject.

More particularly, a subject affected by a psychiatric disorder or disease involving mood disturbance, more particularly mood depression, has a lower capacity to discriminate a mixture, which contains at least two different odorants in a certain proportion, from a mixture, which contains the same at least two different odorants but in a different proportion, i.e., has a lower capacity to discriminate between two mixtures or compositions that belong to the same functional association of the application.

The lower the capacity of the subject the higher the severity of the psychiatric disease.

As mentioned above (and as apparent from the examples below), the capacity of discriminating between mixtures of the same functional association is indicative of, or positively correlates with, the olfactory capacity, more particularly the olfactory discrimination capacity of said subject.

For example:
a subject (subject n° 1) discriminates between the (at least) two mixtures or compositions of a first functional association, which comprise said odorants at certain proportions (e.g., at 8/2 and 2/8 proportions, respectively) [discrimination test n° 1], but does not discriminate between the (at least) two mixtures or compositions of a second functional association, which comprise said odorants at proportions, which are closer to each other (e.g., at 6/4 and 4/6 proportions) [discrimination test n° 1],
whereas
the same subject (subject n° 1) did not succeed in any of the two discrimination tests [discrimination tests n° 1 and n° 2] before he/she received antidepressant treatment.

In this example, it can be concluded that subject n° 1 is responsive to the antidepressant treatment.

Another example is the following example:
a subject (subject n° 1) discriminates between the (at least) two mixtures or compositions of a first functional association, which comprise said odorants at certain proportions (e.g., at 8/2 and 2/8 proportions, respectively) [discrimination test n° 1], but does not discriminate between the (at least) two mixtures or compositions of a second functional association, which comprise said odorants at proportions, which are closer to each other (e.g., at 6/4 and 4/6 proportions) [discrimination test n° 1],
whereas
another subject (subject n° 2) does not succeed in any of the two discrimination tests [discrimination tests n° 1 and n° 2].

In this example, it can be concluded that the severity of the psychiatric disease of subject n° 2 is higher than the severity of the psychiatric disease of subject n° 1.

A method or use of the application is advantageously performed in a subject in need thereof.

Said subject is a mammal as above described, more particularly a human, still more particularly a diseased human, still more particularly a diseased human affected by or suspected of being affected by a psychiatric disorder or disease involving mood disturbance, more particularly mood depression.

According to an aspect of the application, said subject is at a stage where he/she does not show the symptoms of a severe stage of psychiatric disorder or disease involving mood disturbance, more particularly mood depression.

Advantageously, said subject does not show or does not have severe depression. More particularly, the subject may show minimal, mild or moderate depression, more particularly minimal or mild depression.

For example, according to the BDI-II test, said subject may score less than 29 (moderate, mild or minimal depression), more particularly less than 20 (mild or minimal depression), still more particularly less than 14 (minimal depression).

Said applications notably comprise the use of said at least one product of the application in the diagnosis, more particularly in the in vivo diagnosis of a psychiatric disorder or disease involving mood disturbance, more particularly mood depression.

According to an aspect of the application, said use in the (in vivo) diagnosis of a psychiatric disorder or disease involving mood disturbance, more particularly mood depression, further comprises determining whether said subject has a reduced olfactory capacity, more particularly a reduced olfactory discrimination capacity, compared to a healthy and normosmic control subject. A reduced olfactory capacity, more particularly a reduced olfactory discrimination capacity, is indicative of a psychiatric disorder or disease involving mood disturbance, more particularly mood depression. The extent of reduction of olfactory capacity, more particularly of olfactory discrimination capacity, is indicative of, or positively correlates with, the severity of mood disturbance, more particularly of mood depression, in said subject.

Said applications notably comprise the use of said at least one product of the application to determine or measure the severity of a psychiatric disorder or disease that involves mood disturbance, more particularly depression. Said applications more particularly comprise the use of said at least one product of the application in the diagnosis, more particularly the in vivo diagnosis of the severity of a psychiatric disorder or disease that involves mood disturbance, more particularly mood depression.

According to an aspect of the application, said use in determining and/or measuring the severity of a psychiatric disorder or disease that involves mood disturbance, more particularly mood depression, and/or said use in the (in vivo) diagnosis of the severity of a psychiatric disorder or disease that involves mood disturbance, more particularly mood depression, further comprise(s) determining and/or measuring the extent of reduction in olfactory discrimination capacity of said subject. The higher said extent the higher said severity.

Said applications notably comprise the use of said at least one product of the application in the treatment of a psychiatric disorder or disease involving mood disturbance, more particularly mood depression.

According to an aspect of the application, said use in the treatment of a psychiatric disorder or disease involving mood disturbance, more particularly mood depression, further comprises selecting a treatment, more particular an antidepressant treatment, which increases the olfactory capacity, more particularly the olfactory discrimination capacity, of said subject, and administering said selected treatment (or antidepressant treatment) to said subject.

According to an alternative or complementary aspect of the application, said use in the treatment of a psychiatric disorder or disease involving mood disturbance, more particularly mood depression, further comprises modifying and/or adjusting the nature and/or dosage of the treatment given or applied to the patient so as to increase the olfactory capacity, more particularly the olfactory discrimination capacity, of said subject.

Said applications notably comprise the use of said at least one product of the application in determining and/or measuring and/or monitoring the efficiency of a treatment that is intended for treating a psychiatric disorder or disease involving mood disturbance, more particularly depression. More particularly, said applications notably comprise the use of said at least one product of the application in the diagnosis, more particularly the in vivo diagnosis, of response or non-response (or resistance) to a treatment that is intended for treating a psychiatric disorder or disease involving mood disturbance, more particularly mood depression.

According to an aspect of the application, said use in the (in vivo) diagnosis of response or non-response (or resistance) to a treatment that is intended for treating a psychiatric disorder or disease involving mood disturbance, more particularly mood depression, further comprises submitting a subject, who has received said treatment, to said sequential smelling or sniffing, and determining whether said treatment increases or decreases the olfactory discrimination capacity of said subject. An increased olfactory discrimination capacity is indicative of response to said treatment. A reduced or unmodified (e.g., non-significantly different) olfactory discrimination capacity is indicative of non-response (or resistance) to said treatment.

According to an aspect of the application, said use in the (in vivo) diagnosis of response or non-response (or resistance) to a treatment that is intended for treating a psychiatric disorder or disease involving mood disturbance, more particularly mood depression, further comprises:
  administering a candidate antidepressant treatment to said subject,
  placing said subject in smelling or sniffing contact with said at least one product of the application,
  determining whether said candidate antidepressant treatment increases the olfactory capacity, more particularly the olfactory discrimination capacity, of said subject.

Said subject can be diagnosed to be non-responsive (or resistant) to said candidate antidepressant treatment if said olfactory capacity, more particularly said olfactory discrimination capacity, is not increased. Said subject can be diagnosed to be responsive to said candidate antidepressant treatment if said olfactory capacity, more particularly said olfactory discrimination capacity, is increased.

Said treatment can e.g., be a pharmaco-therapeutic treatment, e.g., a treatment comprising the administration of at least one Selective Serotonin Reuptake Inhibitor (SSRI) and/or at least one Serotonin and Noradrenalin Reuptake Inhibitor (SNRI), for example the administration of PROZAC®.

Alternatively or complementarily, said treatment can be a treatment comprising the administration of electroshock(s), e.g., electroconvulsivotherapy Said applications notably comprise the use of said at least one product of the application to measure the olfactory capacity, more particularly the olfactory discrimination capacity of a subject.

Said applications notably comprise the use of said at least one product of the application to identify a treatment suitable for (or useful in) treating a psychiatric disorder or disease that involves mood disturbance, more particularly mood depression. Said use may comprise:
  using at least one product of the application to measure the olfactory discrimination capacity of a subject affected by a psychiatric disorder or disease that involves mood disturbance, more particularly mood depression,
  submitting said subject to a candidate antidepressant treatment,
  determining whether said candidate treatment lessen the severity of said psychiatric disorder or disease in said subject,
whereby said candidate antidepressant treatment is identified as suitable for (or useful in) treating a psychiatric disorder or disease that involves mood disturbance, more particularly mood depression.

In the implementation of this use, said subject may advantageously be a non-human mammal, more particularly a rodent, such as a mouse.

The application also relates to a method of manufacturing a device useful in or for the diagnosis or the treatment of a psychiatric disorder or disease that involves mood disturbance, more particularly depression, which comprises:

producing at least one mixture or composition of the application, or at least two different mixture(s) or composition(s) of the application, or at least one functional association of the application, or at least one kit comprising at least one functional association of the application, or at least one collection of at least two functional associations of the application, or at least one kit comprising at least one collection of the application, placing said at least one mixture or composition in or on a device, which comprises a structure for dispensing the odor or scent emitted by said mixture(s) or composition(s), and which is adapted to sniffing or smelling the emitted odor or scent by a mammal, more particularly in or on an odor dispensing device for assessing nasal chemosensory performance.

The application also relates to the device obtainable by, or obtained by said method of manufacture.

In the application, unless specified otherwise or unless a context dictates otherwise, all the terms have their ordinary meaning in the relevant field(s).

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In an attempt to help the reader of the present application, the description has been separated in various paragraphs or sections. These separations should not be considered as disconnecting the substance of a paragraph or section from the substance of another paragraph or section. To the contrary, the present description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Example 1: Olfactory Test on a Non-Human Mammal Model

We investigated olfaction in an animal model of depression: the CORT model (David et al. 2009, Neuron 62(4): 479-493, including Supplemental Data). This model is based on the disruption of the equilibrium of the hypothalamo-pituitary-adrenal (HPA) axis, reminiscent of what can be observed in human subjects diagnosed with Major Depressive Disorder (MDD). The model involves chronic administration of a low dose of corticosterone in mice, inducing a high anxiety- and depressive-like behavioral state that are both reversed by antidepressant treatment and are associated with an enhancement of adult hippocampal neurogenesis.

We assessed odorant perception, discrimination and memory, using operant discrimination paradigms in automated olfactometers. We found an alteration of olfactory perception in CORT mice that was reversed by antidepressant treatment. Furthermore, we found a significant correlation between the perception threshold of n-butanol and the level of depression assessed by the splash test.

Moreover, we found an alteration in the discrimination of mixtures of odorants, more particularly of binary mixtures of monomolecular odorants, in both non-treated and antidepressant drug-treated CORT mice, demonstrating that fine discrimination of odorants is disrupted in this animal model of depression and is not rescued by antidepressant treatment.

Methodology

1. Animals

C57BL/6 male mice from Taconic Farms, Inc. (Tombjergvej 40, DK-4623 Lille Skensved, Denmark) were administered corticosterone (CORT, 5 mg/kg/day in drinking water) for one month, to induce an anxiety/depression-like state. Depression-like behavior was checked by the splash test, the open field test, elevated plus maze and novelty suppressed feeding.

Figure 1:
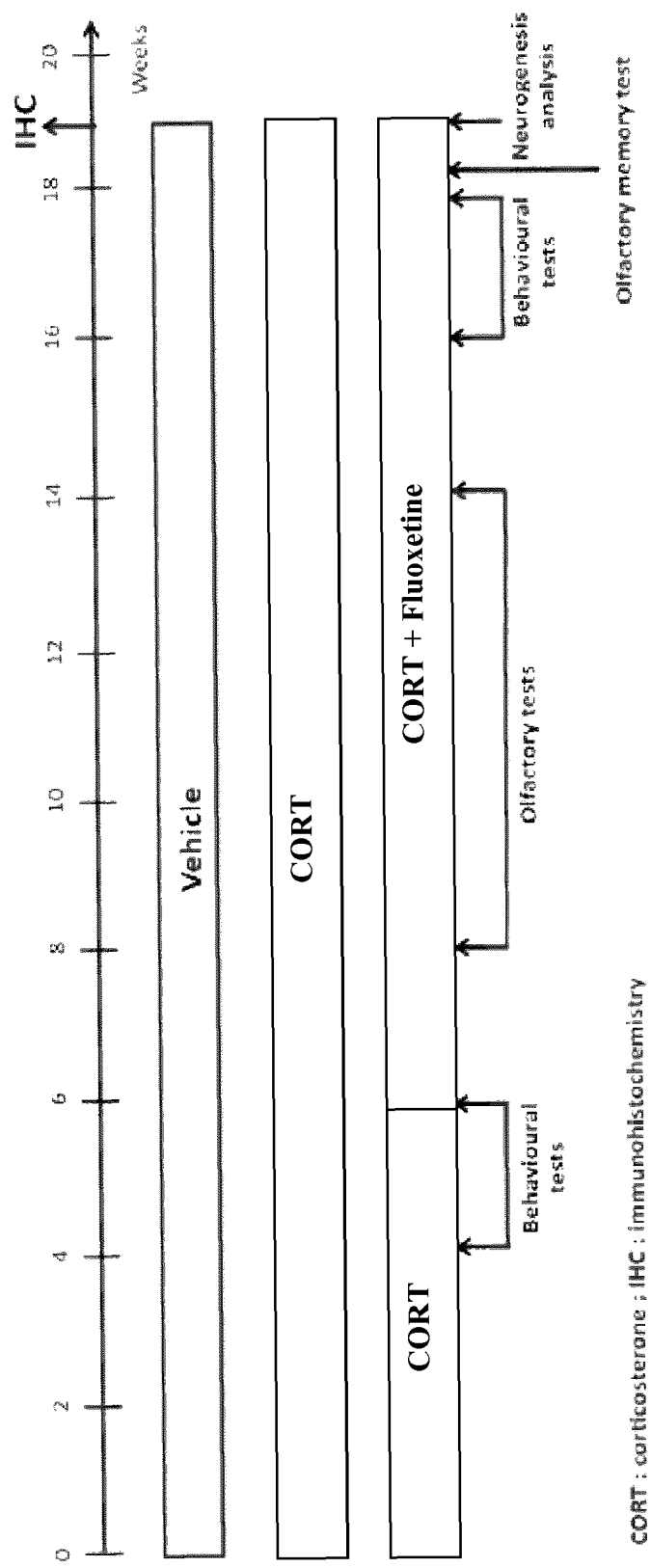
FIG. 1: diagrammatic representation of an experimental design.
CORT=corticosterone; IHC=immunohistochemistry;
first bar (on the top)=vehicle;
penultimate bar (in the middle)=CORT.

Then, 29 of these mice were put on a chronic fluoxetine regimen (FLX: 5 mg/kg/day in drinking water, with CORT, 5 mg/kg/day, named CORT+FLX mice), as previously described (David et al. 2009, Neuron 62(4): 479-493, including Supplemental Data), while 8 mice continued to receive corticosterone chronically (named CORT mice) [cf. FIG. 1]. Moreover, 8 control mice received the vehicle only (named VEHICLE mice) [cf. FIG. 1].

2. Behavioral Testing 2.1. Assessment of the Depressive State

Depression related changes include decreased self care, a behavior that can be evaluated by the splash test (David et al. 2009, Neuron 62(4): 479-493, including Supplemental Data). This test consists in squirting 200 microliters of a 10% sucrose solution on the mouse back. The grooming latency, frequency and duration are then recorded. About 90% of C57BL/6 mice demonstrate depression-related signs in response to chronic corticosterone.

2.2. Assessment of Olfaction

Odorants.

All odorants are monomolecular compounds from Sigma-Aldrich (Sigma-Aldrich Chemie S.a.r.l.; L'Isle d'Abeau Chesnes; 38297 Saint-Quentin Fallavier; France), dissolved in water or mineral oil as indicated below.

Automated Olfactometers.

Mice were partially water-deprived by receiving 1-2 mL/day of water for one week and then trained on a "go-out" discrimination task in computer-controlled eight-channel olfactometers (Lazarini et al. 2009, PlosOne 4(9): e7017). They were trained to respond to the presence of an odorant solution (positive stimulus, S+) diluted in a solvent, like water or mineral oil, by licking the water delivery tube situated out of the odorant sampling port (5 cm distance). They were also trained not to respond on the presentation of another odorant or solvent (negative stimulus, S−). A single stimulus (S+ or S−) was presented at each trial. S+ and S− trials were carried out in random order such that an equal number of each type of trial occurred in each series (named block) of 20 trials and that one type of trial did not occur more than three consecutive times. As described in Lazarini et al. 2009 (PlosOne 4(9): e7017), licking response following an S+ trial and no licking following an S− trial were scored as correct, and named hit and correct rejection respectively [cf. FIG. 2]. In the case of a hit, about 10 μL of water were offered as a reward. A licking response following an S− trial and no licking following an S+ trial were scored as error and named false alarm and miss respectively. Accuracy (percentage of correct responses) was scored for each block of 20 trials [(hits+correct rejections)/20×100]. Olfactory performances were determined using monomolecular odorant compounds and binary odorant mixtures. Mice underwent a session of 8 blocks per day. All odorants were diluted in water or mineral oil just before the experiments, and their concentrations are given as the dilution of the odorant in the saturator bottles. Mice were initially trained to discriminate between isoamylacetate (IAA, dilution $10^{-3}$ in water, S+) and water (S−).

Odorant mixture discrimination tasks. Mice were trained to distinguish between 0.1% carvone + (S+) and carvone − (S−) diluted in mineral oil (simple discrimination task).

Then, olfactory discrimination performance was determined for two carvone mixture tasks (difficult discrimination task) as follows:
  in the first task:
  S+ was a solution of 0.8% carvone + and 0.2% carvone − and
  S− was a solution of 0.2% carvone + and 0.8% carvone −;
  in the second task:
  S+ was a solution of 0.6% carvone + and 0.4% carvone − and
  S− was a solution of 0.4% carvone + and 0.6% carvone −.
Odorant Detection Threshold.

Mice were trained in the olfactometer to detect successively descending decimal concentrations of n-butanol (S+) diluted in water. Each concentration was tested daily in 8 blocks of 20 trials. In each session, water served as the S−. Mice were given one to two sessions per day (morning, afternoon) with one decimal dilution of the odorant per session. A maximum of 16 blocks per day was allowed (2 sessions of 8 blocks). The session stopped at the criterion performance achievement (>90% of correct response in the block). If the criterion performance was not achieved in two successive sessions with the same odorant dilution, the preceding dilution was considered as the detection threshold.

Results

1. Depressive-Like Behavior

We assessed the grooming behavior of mice using the splash test that consists in squirting a sucrose solution on the mouse back and measuring the latency to groom, the number of grooming sessions as well as total grooming duration. This test has been described as a well-validated index of a depressed-like state (David et al. 2009, Neuron 62(4): 479-493, including Supplemental Data). We observed that mice that were administered the chronic treatment with CORT showed a significantly increased latency to groom compared to animals that received the vehicle (116.1±17.9 vs 29.1±7.5 s, P<0.001) [cf. FIG. 3A]. Moreover, compared to vehicle-treated animals, grooming duration was decreased in CORT-treated mice (43.7±5.5 vs 80.5±8.5, P<0.05) [cf. FIG. 3B] as well as grooming frequency (2.8±0.3 vs 5.9±0.7, P<0.05) [cf. FIG. 3C]. In an interesting manner, a 2-month fluoxetine treatment (18 mg/kg/day) was able to decrease grooming latency (26.6±4.1 s, P<0.001 vs CORT-treated) [cf. FIG. 3A] and increase grooming duration (92.2±8.9, P<0.05 vs CORT-treated) [cf. FIG. 3B] and frequency (6.1±0.5, P<0.05 vs CORT-treated) [cf. FIG. 3C]. Taken together, these data indicate that chronic antidepressant treatment is able to attenuate a standard anxiety/depression-like phenotype induced by excess glucocorticoids.

It is worth noting that mice showed depression-related symptoms in response to chronic corticosterone when tested in other standardized behavioral tests of depression (open field test, elevated plus maze and novelty suppressed feeding, tail suspended test, forced swim test, data not shown). Interestingly, chronic fluoxetine administration in CORT-treated mice reversed these symptoms.

2. Olfactory Discrimination and Detection

As shown in FIG. 4A, chronic treatment with CORT alone or CORT and fluoxetine did not alter the ability of mice to discriminate between the two similar carvone isoforms in the simple olfactory discrimination task, since the acquisition rate was similar for all groups. A score of 50% corresponds to the success rate expected on the basis of chance alone (dashed line, FIG. 4A). However, in the difficult discrimination task of carvone mixtures, the performance of CORT animals was significantly poorer compared to vehicle-treated animals (P<0.01 for the 8/2 vs 2/8 mixture and P<0.05 for the 6/4 vs 4/6 mixture). Chronic administration of fluoxetine was not able to restore that deficit.

Moreover, the results of our olfactory detection test revealed that chronic CORT treatment induces a significant decrease in the detection threshold of around two orders of magnitude (5.7±0.3 vs 7.4±0.4, P<0.01 vs vehicle-treated). Interestingly, chronic fluoxetine treatment was able to restore the threshold in CORT-treated animals (7.3±0.3, P<0.05 vs CORT-treated) (FIG. 4B).

3. Correlation Between Depressive State and Olfactory Detection Threshold

Our results revealed that the degree of certain depressive-like symptoms is significantly correlated to the olfactory threshold score [cf. FIGS. 5A and 5B]. More precisely, the olfactory threshold is negatively correlated to the latency to groom in the splash test ($r^2$=0.18; P=0.004; n=44) and positively correlated to the number of grooming sessions ($r^2$=0.13; P=0.017; n=43).

4. Long-Term Olfactory Memory

We assessed the ability of CORT animals to remember two odorants learned one month before. To assess olfactory memory, vehicle, CORT and CORT+FLX mice were trained during 5 consecutive days in order to recall to distinguish between 1% carvone (+) and 1% carvone (−). Carvone (+) was the rewarded stimulus and carvone (−) was the unrewarded stimulus. Mice were then retested for the carvone discrimination task at 30 days (t30) following the end of the training session (t0) (FIG. 6A). In this second session, no reward was given for correct responses. We assessed the percentage of correct responses for the three groups during the last block of the acquisition period (t0) and during the first block of the memory task performed 30 days later (t30, FIG. 6A). All the three groups of mice had at least 90% correct responses in the last block of training (acquisition: t0; FIG. 6A), indicating that they were all able to acquire odorant-associated memory. However, a significant difference in performance was observed between sessions. Performance accuracy was significantly lower in the second session for CORT mice when compared to vehicle-treated mice and CORT+FLX animals (% correct response, vehicle: 71.25±3.62, CORT: 51.88±2.66, CORT+FLX: 61.35±2.88). Bonferonni post-hoc test: ***: P<0.001 between vehicle and CORT-treated, *: P<0.05 between CORT and CORT+FLX).

Thus, memory of learned odorants was better retained over a 30-day period in vehicle-treated compared to CORT mice. CORT-treated animals exhibited a memory deficit that was significantly attenuated by FLX.

5. Correlation Between Depressive State and Long-Term Olfactory Memory

Our data demonstrated that the degree of certain depressive-like symptoms is significantly correlated to the olfactory memory score [cf. FIGS. 6B]. Long-term olfactory memory is positively correlated with grooming frequency in the Splash test. (Pearson's test, $r2=0.11$; **$P=0.03$; $n=42$).

Conclusion and Perspectives

Our findings in the CORT mice model show that the olfactory perception threshold correlates with the depressive state.

Moreover, we demonstrate that both depressed and antidepressant-treated depressed mice perform poorly in the task that involves fine discrimination of mixtures of odorants, more particularly of binary mixtures of monomolecular odorants: cf. FIG. 4A.

The experiment, which is above described, can be performed with mixtures of odorants other than the mixtures of carvone + and carvone −, for example, with:
  mixtures of isoamylacetate and of anethol, e.g., at 8/2 and 2/8 proportions;
  mixtures of anethol and of eugenol, e.g., at 8/2 and 2/8 proportions.

Odorants are considered safe and are used in food and cosmetic products.

Therefore, the test can easily be implemented in humans (cf. example 2 below).

Example 2: Olfactory Test on Humans

The data obtained in the animal model (cf. example 1) allowed us to propose an olfactory test for major depression in humans, based on the discrimination of mixtures of at least two odorants, more particularly on the discrimination of mixtures of at least two monomolecular odorants.
  Examples of mixtures include (cf. example 1 above):
  mixtures of carvone + and of carvone −, e.g., at 8/2 and 2/8 proportions;
  mixtures of isoamylacetate and of anethol, e.g., at 8/2 and 2/8 proportions;
  mixtures of anethol and of eugenol, e.g., at 8/2 and 2/8 proportions.

Odorants can for example be presented in sniffing sticks, such as described in Hummel et al. 1997 (Chem. Senses 22: 39-52) and commercialized as SNIFFIN' STICKS™ by Burghardt Messtechnik GmbH (Tinsdaler Weg 175, D-2280 Wedel, Germany), e.g., (4 mL) sniffing sticks containing the odorant mixture in a solvent, such as 2 phenyl ethanol. The mixture discrimination test can optionally be associated with the detection threshold test (odorant perception test e.g., with n-butanol or phenylethylalcohol; cf. Hummel et al. 1997, Chem. Senses 22: 39-52; cf. Negoias et al. 2010, Neuroscience 169(1): 415-421). For the discrimination of mixtures, three sticks can be presented to the subject: two sticks contain the same odorant mixture (e.g., a mixture of carvone + and of carvone − at 8/2 proportion in a solvent such as 2 phenyl ethanol) and the third tick contains a different associated odorant mixture (e.g., a mixture of carvone + and of carvone − at 2/8 proportion in the same solvent). The subject is requested to indicate the stick which smells different.

For the threshold assessment, two sticks can be presented to the subject: one stick contains the solvent and the other stick contains a dilution of n-butanol or phenylethylalcohol (in increasing concentrations, e.g., in increasing 2-fold concentrations, e.g., starting from 0.4% vol/vol in propylene glycol).

For example, the mixture discrimination test can be implemented on a population of humans diagnosed with Major Depressive Disorder (MDD), more particularly on:
  MDD humans, who have received an anti-MDD treatment and are responsive to the treatment,
  MDD humans, who have received an anti-MDD treatment and are resistant or non-responsive to the MDD treatment, and
  MDD patients, who do not have received an anti-MDD treatment yet.

The mixture discrimination capacity of this population, more particularly of each of these three sub-populations, can be compared to the discrimination capacity of healthy humans, more particularly of normosmic healthy humans.

The mixture discrimination test is useful for assessing the degree of depression and the response/resistance to antidepressant drugs. This test can optionally be associated with the detection threshold test, and is notably useful:
  for the (early) diagnosis of mood disorders, more particularly Major Depressive Disorder (or Major Depressive Episode),
  for monitoring or determining the level of efficiency that a treatment has to treat such a disorder or episode (e.g., SSRI and/or SNRI treatment) and/or for detecting response or non-response/resistance to such a treatment.

BIBLIOGRAPHIC REFERENCES

Scientific Publications:
Cain et al. 1988, Laryngoscope 98:83-88;
Cain 1989, Ear Nose Throat J. 68: 316, 322-328;
David et al. 2009, Neuron 62(4): 479-493 [including Supplemental Data];
Doty et al. 1984, Physiol. Behav. 32: 489-502;
Doty et al. 1984, Laryngoscope 94 (2Pt1): 176-178
Doty et al. 1996, Laryngoscope 106 (3Pt1): 353-356,
Hummel et al. 1997, Chem. Senses 22: 39-52;
Hummel et al. 2001, Ann. Otol. Rhinol. and Laryngol. 110: 976-981;
Hummel et al. 2007, Eur. Arch. Otorhinolaryngol. 364(3): 237-243;
Kobal et al. 1996, Rhinology 34: 222-226;
Kobal et al. 2000, Eur. Arch. Otorhinolaryngol. 257: 205-211;
Lazarini et al. 2009, PlosOne 4(9): e7017;
Negoias et al. 2010, Neuroscience 169(1): 415-421;
Pause et al. 2001, Journal of Psychiatric Research 35: 271-277;
Pollatos et al. 2007, Journal of Affective Disorders 102: 101-108.

Reference Manuals or Database:
The "BECK DEPRESSION INVENTORY®" (BDI): Beck, A. T., Steer, R. A., & Brown, G. K. 1996, "Manual for the Beck Depression Inventory-II", San Antonio, Tex.: The Psychological Corporation, U.S.A., more particularly the BDI-II edition published in 1996;
«The Diagnostic and Statistical Manual of Mental Disorders» (DSM), edited by the American Psychiatric Association e.g., the DMS-IV-TR or DSM-V edition;
the Arctander atlas (Arctander S. "*Perfume and flavor chemicals*: (*aroma chemicals*)", Allured Publishing Corporation, Carol Stream Ill., 1994);

the OdorDB database (Yale Center for Medical Informatics, U.S.A.) available on http://senselab.med.yale.edu/odordb/eavObList.aspx?db=5&c1=1.

The invention claimed is:

1. A method of production of a kit, which is suitable for diagnosing a psychiatric disorder or disease involving mood depression, or for diagnosing the severity of a psychiatric disorder or disease, which involves mood depression, wherein said method comprises
mixing odorant compounds in a pharmaceutically suitable and odorless vehicle to produce a first composition, wherein said odorant compounds consist of at least two different odorant compounds selected from the group consisting of selected from the group consisting of R-carvone, S-carvone, isoamylacetate, anethol, eugenol, 2-phenylethanol, geraniol, linalool, cineole, D-limonene, L-limonene, menthol, and cinnamon aldehyde,
mixing odorant compounds in a pharmaceutically suitable and odorless vehicle to produce a second composition, wherein said odorant compounds consist of at least two different odorant compounds,
mixing odorant compounds in a pharmaceutically suitable and odorless vehicle to produce a third composition, wherein said odorant compounds consist of at least two different odorant compounds,
wherein the odorant compounds of said first composition are the same odorant compounds as the odorant compounds of said second composition, and are the same odorant compounds as the odorant compounds of said third composition,
wherein the proportion of the odorant compounds with respect to each other in said first composition is different from their proportion in said second composition and different from their proportion in said third composition,
wherein the proportion of the odorant compounds with respect to each other in said second composition is identical to their proportion in said third composition,
wherein said method further comprises placing said first, second and third compositions each separately in an odor dispensing device for assessing nasal chemosensory performance to produce a first odor dispensing device, a second odor dispensing device and a third odor dispensing device, respectively, and combining said first, second and third odor dispensing devices in a kit.

2. The method of claim 1, wherein each of said first, second and third odor dispensing devices is a felt-tip pen suitable for assessing nasal chemosensory performance, which contains said first, second or third composition, respectively, in a reservoir or absorbent material associated with the felt tip of the pen to dispense the odorants of said composition through said felt tip.

3. The method of claim 1, wherein said kit further comprises instructions to use said first, second and third odor dispensing devices for sequential smelling or sniffing of said first, second and third compositions, respectively, by a subject in need of diagnosis of a psychiatric disorder or disease involving mood depression or in need of diagnosis of the severity of a psychiatric disorder or disease, which involves mood depression.

4. The method of claim 1, wherein said kit further comprises instructions to use said first, second and third odor dispensing devices for sequential smelling or sniffing of said first, second and third compositions, respectively, by a subject in need of diagnosis of a psychiatric disorder or disease involving mood depression or in need of diagnosis of the severity of a psychiatric disorder or disease, which involves mood depression, and instructions to detect whether said subject has a lower olfactory capacity to discriminate said first composition from said second and third compositions.

5. The method of claim 1, wherein said third composition is a duplicate of said second composition.

6. The method of claim 1, wherein said first composition contains said odorant compounds in a proportion that is consciously perceived by a healthy normosmic human as emitting an odor or scent that is different from the odor or scent emitted by said second and third compositions.

7. The method of claim 1, wherein said pharmaceutically suitable and odorless vehicle is an odorless liquid solvent.

8. The method of claim 1, wherein each of said at least two different odorant compounds is selected from the group consisting of R-carvone, S-carvone, isoamylacetate, anethol and eugenol.

9. The method of claim 1, wherein said subject is affected by, or suspected of being affected by a Major Depressive Disorder (MDD).

10. A kit produced by the method of claim 1.

11. A method for diagnosing a psychiatric disorder or disease involving mood depression in a subject in need thereof, wherein said method comprises sequential smelling or sniffing by said subject of a first composition, of a second composition and of a third composition,
wherein each of said first, second and third compositions comprises odorant compounds, which consist of at least two different odorant compounds selected from the group consisting of selected from the group consisting of R-carvone, S-carvone, isoamylacetate, anethol, eugenol, 2-phenylethanol, geraniol, linalool, cineole, D-limonene, L-limonene, menthol, and cinnamon aldehyde,
wherein the odorant compounds of said first composition are the same odorant compounds as the odorant compounds of said second composition, and are the same odorant compounds as the odorant compounds of said third composition,
wherein the proportion of the odorant compounds with respect to each other in said first composition is different from their proportion in said second composition and different from their proportion in said third composition,
wherein the proportion of the odorant compounds with respect to each other in said second composition is identical to their proportion in said third composition,
wherein said method further comprises detecting whether said subject has a lower olfactory capacity to discriminate said first composition from said second and third compositions compared to a healthy and normosmic control subject, and wherein a lower olfactory discrimination capacity is indicative of a psychiatric disorder or disease involving mood depression.

12. The method of claim 11, wherein said third composition is a duplicate of said second composition.

13. The method of claim 11, wherein said first composition contains said odorant compounds in a proportion that is consciously perceived by a healthy normosmic human as emitting an odor or scent that is different from the odor or scent emitted by said second and third compositions.

14. The method of claim 11, wherein the odorant compounds of said first composition are in mixture with an odorless liquid solvent, wherein the odorant compounds of said second composition are in mixture with an odorless liquid solvent and wherein the odorant compounds of said third compositions are in mixture with an odorless liquid solvent.

15. The method of claim 11, wherein said first, second and third compositions are each separately contained in an odor dispensing device for assessing nasal chemosensory performance.

16. The method of claim 11, wherein said first, second and third compositions are each separately contained in an odor dispensing device for assessing nasal chemosensory performance, and wherein said odor dispensing device is a felt-tip pen suitable for assessing nasal chemosensory performance, which contains said composition in a reservoir or absorbent material associated with the felt tip of the pen to dispense the odorants of said composition through said felt tip.

17. The method of claim 11, wherein each of said at least two different odorants is selected from the group consisting of R-carvone, S-carvone, isoamylacetate, anethol and eugenol.

18. The method of claim 11, wherein said subject is affected by, or suspected of being affected by a Major Depressive Disorder (MDD).

19. A method for diagnosing the severity of a psychiatric disorder or disease, which involves mood depression in a subject in need thereof, wherein said method comprises sequential smelling or sniffing by said subject of a first composition, of a second composition and of a third composition, wherein each of said first, second and third compositions comprises odorants, which consist of at least two different odorant compounds selected from the group consisting of selected from the group consisting of R-carvone, S-carvone, isoamylacetate, anethol, eugenol, 2-phenylethanol, geraniol, linalool, cineole, D-limonene, L-limonene, menthol, and cinnamon aldehyde, wherein the odorant compounds of said first composition are the same odorant compounds as the odorants of said second composition, and are the same odorant compounds as the odorant compounds of said third composition, wherein the proportion of the odorant compounds with respect to each other in said first composition is different from their proportion in said second composition and different from their proportion in said third composition, wherein the proportion of the odorant compounds with respect to each other in said second composition is identical to their proportion in said third composition, wherein said method further comprises determining the extent at which the olfactory capacity to discriminate said first composition from said second and third compositions is reduced in said subject compared to a healthy and normosmic control subject, and wherein the higher said extent the higher said severity.

* * * * *